(12) United States Patent
Gargano et al.

(10) Patent No.: US 7,648,549 B2
(45) Date of Patent: Jan. 19, 2010

(54) METHOD, SYSTEM AND APPARATUS FOR DETECTING DEFECTS IN A HONEYCOMB BODY USING A PARTICULATE FLUID

(75) Inventors: Patrick Michael Gargano, Addison, NY (US); Babak Robert Raj, Elmira, NY (US); William Paul Ryszytiwskyj, Big Flats, NY (US); Michael George Shultz, Big Flats, NY (US); David John Worthey, Elmira, NY (US); Leon Robert Zoeller, III, Hammondsport, NY (US)

(73) Assignee: Corning Incorporated, Corning, NY (US)

( * ) Notice: Subject to any disclaimer, the term of this patent is extended or adjusted under 35 U.S.C. 154(b) by 422 days.

(21) Appl. No.: 11/494,880

(22) Filed: Jul. 28, 2006

(65) Prior Publication Data
US 2007/0022724 A1    Feb. 1, 2007

Related U.S. Application Data

(60) Provisional application No. 60/704,171, filed on Jul. 29, 2005.

(51) Int. Cl.
*B01D 39/20*    (2006.01)

(52) U.S. Cl. ............... 55/523; 55/524; 55/DIG. 30; 55/385.3; 95/273

(58) Field of Classification Search ............... 55/523, 55/524, 385.3, DIG. 30; 95/273; 96/414, 96/417, 422; 73/19.01, 19.04, 19.12, 23.01, 73/23.2, 40, 40.7; 210/348, 510.1; 356/237.1, 356/337, 402; 374/1, 4
See application file for complete search history.

(56) References Cited

U.S. PATENT DOCUMENTS 4,055,075 A    10/1977    Allan et al. ................. 73/40.7

(Continued)

FOREIGN PATENT DOCUMENTS

EP    0 539 202    4/1993

(Continued)

OTHER PUBLICATIONS

Shoshin Y et al; "Production of well-controlled laminar aerosol jets and their application for studying aerosol combustion processes"; Aerosol Sci. Technol.; Aerosol Science and Tehcnology, Sep. 2002; vol. 36, No. 9; pp. 953-962.

*Primary Examiner*—Michael A Marcheschi
*Assistant Examiner*—Karla Hawkins
(74) *Attorney, Agent, or Firm*—Matthew B. McNutt

(57) ABSTRACT

A system, apparatus and method for detecting defects in a honeycomb body. The system and apparatus include a fixture adapted to hold the honeycomb body, a particulate fluid source, a pipe which defines a flow path between the particulate fluid source and a first end face of the honeycomb body thereby allowing particulate fluid to flow from the particulate fluid source to the first end face of the honeycomb body. The particulate fluid emerges at a second end face of the honeycomb body through defects, if any, in the honeycomb body where the positions of such defects may be monitored. The system and apparatus includes a flow straightener disposed in the flow path to minimize boundary layer influence of the pipe on the flow of the particulate fluid. A substantially uniform velocity flow profile is provided to the first end face of the honeycomb body.

25 Claims, 7 Drawing Sheets

U.S. PATENT DOCUMENTS

| | | | |
|---|---|---|---|
| 4,390,355 A * | 6/1983 | Hammond et al. | 55/523 |
| 4,515,007 A | 5/1985 | Herman | 73/38 |
| 4,619,136 A | 10/1986 | Ortiz | 73/38 |
| 4,676,092 A | 6/1987 | Tuttle | 73/38 |
| 5,102,434 A | 4/1992 | Hijikata et al. | 55/97 |
| 5,205,156 A | 4/1993 | Asano et al. | 73/38 |
| 5,398,541 A | 3/1995 | Hijikata et al. | 73/38 |
| 5,640,236 A | 6/1997 | Nagashima | 356/237 |
| 6,666,070 B1 | 12/2003 | Hagg et al. | 73/38 |
| 6,840,083 B2 | 1/2005 | Hijikata | 73/12.01 |
| 7,012,678 B2 | 3/2006 | Enomoto et al. | 356/237.1 |
| 7,043,964 B1 | 5/2006 | Hickman | 73/40 |
| 2003/0112437 A1 * | 6/2003 | Enomoto et al. | 356/402 |
| 2004/0000186 A1 | 1/2004 | Hagg et al. | 73/38 |
| 2004/0050915 A1 * | 3/2004 | Goenka et al. | 228/248.1 |
| 2006/0137525 A1 | 6/2006 | Rae et al. | 95/273 |
| 2006/0151926 A1 | 7/2006 | Zoeller, III | 264/603 |
| 2006/0174695 A1 | 8/2006 | Miyashita et al. | 73/38 |

FOREIGN PATENT DOCUMENTS

| | | |
|---|---|---|
| EP | 0 569 754 | 11/1993 |
| EP | 1 296 125 | 3/2003 |
| EP | 1 607 734 | 12/2005 |
| JP | 10-202279 | 1/1997 |
| JP | 2001-165847 | 12/1999 |
| JP | 2000 171024 | 6/2000 |
| JP | 2004 286703 | 10/2004 |
| SU | 798551 | 3/1979 |
| SU | 1250913 | 12/1984 |
| WO | 00/29649 | 5/2000 |
| WO | 2004/056448 | 7/2004 |

* cited by examiner

METHOD, SYSTEM AND APPARATUS FOR DETECTING DEFECTS IN A HONEYCOMB BODY USING A PARTICULATE FLUID

This application claims the benefit of U.S. Provisional Application No. 60/704,171, filed Jul. 29, 2005, entitled "Method, System and Apparatus for Detecting Defects in a Honeycomb Body Using a Particulate Fluid".

FIELD OF THE INVENTION

The invention relates generally to particulate filters. More specifically, the invention relates to a method and apparatus for detecting defects in a honeycomb particulate filter using a particulate fluid.

BACKGROUND OF THE INVENTION

Wall-flow honeycomb filters are used to remove solid particulates from fluids, such as in exhaust gas streams. FIG. 1 illustrates a typical prior art wall-flow honeycomb filter 100. The honeycomb filter 100 has an inlet end face 102, an outlet end face 104, and an array of interconnecting porous walls 106 extending longitudinally from the inlet end face 102 to the outlet end face 104. The interconnecting porous walls 106 define a grid of inlet cells 108 and outlet cells 110. The outlet cells 110 are closed with plugs 112 where they adjoin the inlet end face 102 and open where they adjoin the outlet end face 104. Oppositely, the inlet cells 108 are closed with plugs (not shown) where they adjoin the outlet end face 104 and open where they adjoin the inlet end face 102. Such filters 100 are typically contained in a rigid housing (not shown). Fluid directed at the inlet end face 102 of the honeycomb filter 100 enters the inlet cells 108, flows through the interconnecting porous walls 106 and into the outlet cells 110, and exits the honeycomb filter 100 at the outlet end face 104.

In a typical cell structure, each inlet cell 108 is bordered on one or more sides by outlet cells 110, and vice versa. The inlet and outlet cells 108, 110 may have a square cross-section as shown in FIG. 1 or may have other cell geometry, e.g., rectangle, triangle, hexagon, octagon, etc. Diesel particulate filters are typically made of ceramic materials, such as cordierite, aluminum titanate, or silicon carbide. For diesel particulate filtration, honeycomb filters having cellular densities between about 10 and 300 cells/in$^2$ (about 1.5 to 46.5 cells/cm$^2$), more typically between about 100 and 200 cells/in$^2$ (about 15.5 to 31 cells/cm$^2$), are considered useful in providing sufficient thin wall surface area in a compact structure. Wall thicknesses can vary upwards from the minimum dimension providing structural integrity of about 0.002 in. (about 0.05 mm), but are generally less than about 0.060 in. (1.5 mm) to minimize filter volume. A range of between about 0.010 and 0.030 in (about 0.25 and 0.76 mm) is most often selected for ceramic materials such as cordierite, aluminum titanate, and silicon carbide at the preferred cellular densities.

When particulates, such as soot found in exhaust gas, flow through the interconnecting porous walls 106 of the honeycomb filter 100, a portion of the particulates in the fluid flow stream is retained on or in the interconnecting porous walls 106. The efficiency of the honeycomb filter 100 is related to the effectiveness of the interconnecting porous walls 106 in filtering the particulates from the fluid. Filtration efficiencies up to, or in excess of, 90% by weight of the particulates can be achieved with honeycomb filters having properties such as described above. However, filtration efficiency or integrity of a honeycomb filter can be compromised by manufacturing defects such as holes, cracks, or fissures. Such defects allow the fluid to pass through the filter without proper filtration. Thus, in the production of honeycomb filters for applications such as diesel particulate filtration, it may be desirable to test the honeycomb filters for the presence of such defects that may affect filtration efficiency. Honeycombs with detected defects may be repaired, or if irreparable, discarded.

U.S. Patent Application Publication No. 2003/0112437 (Enomoto et al.) discloses a method of detecting defects in a diesel particulate filter using a particulate, such as smoke. The method involves generating particulates and directing them at an inlet end face of the filter such that the particulates enter the filter. Cells having defects readily allow the particulates inside them to flow into the adjacent cells or through the defective plugs. Thus, numerous, typically larger, particulates emerge at the outlet end face of the honeycomb filter from cells/plugs having defects. A light source, such as a laser source, is positioned to emit light such that the light passes in the vicinity of the filter to irradiate the particulates emerging therefrom. A camera is installed above the filter to photograph reflected beams generated by particulates intersecting the light. Brighter spots in the photographed image correspond to cells/plugs containing defects.

Enomoto et al. discloses, in FIG. 1 thereof, a particulate inlet 6 for providing particulates to the inlet end face of the filter 20. The particulate inlet 6 is a pipe which has the same dimension as the filter and is axially aligned with the filter. When the particulate flows through the pipe, the flow of the particulate fluid near the wall of the pipe may be retarded relative to the flow of the particulate fluid at the center of the pipe due to fluid flow phenomena, thereby possibly leading to cells closer to the periphery of the honeycomb filter receiving less particulates than cells farther away from the periphery of the filter. During testing, defective cells that offer lower resistance to flow will allow more particulates per unit time and larger particulates to pass through them, thereby providing an indication (as between the laser light and the particulates). If a defective cell is starved of flow, and, thus, particulates at the inlet end face, the brightness of the spot indication produced by such a defective cell would be weakened relative to the cells not so starved. Accordingly, such cells would not indicate a defect (or indicate it less dramatically) because of being starved of particulates, even though it is a defective cell.

From the foregoing, there is a desire to avoid ambiguity in test results, particularly at or near the periphery of the tested honeycomb filter.

SUMMARY OF THE INVENTION

In one aspect, the invention is a system for detecting defects in a honeycomb body which comprises a fixture adapted to hold the honeycomb body; a particulate fluid source; a pipe which defines a flow path for particulate fluid between the particulate fluid source and a first end face of the honeycomb body, and a flow straightener including a plurality of vanes disposed in the flow path. When the particulate fluid emerges at a second end face of the honeycomb body, the emerging particles may then be detected by, for example, illumination to identify defects (in walls or plugs) in the honeycomb body. The flow straightener disposed in the flow path minimizes boundary layer influence of the pipe on the flow of the particulate fluid therein. As used herein, the term "particulate fluid" refers to a suspension of solid or liquid particulates in a gaseous medium. Preferably, the particulate fluid is a fog including water particles.

According to another aspect, the invention is an apparatus for applying particulate fluid across an end face of a honeycomb body which comprises a particulate fluid source having a housing with an interior cavity, and a particulate generator which produces particulate fluid; a pipe disposed in the housing and having a first end open to the interior cavity and a second end open to an exterior of the housing wherein a pressure differential drives particulate fluid into the pipe; and a flow straightener comprising a plurality of flow vanes is disposed in the pipe.

In yet another aspect, the invention is a method of detecting a defect in a honeycomb body and comprises the steps of providing a flow of a particulate fluid having a substantially uniform velocity profile to a first end face of a honeycomb body; and detecting particulates emerging from a second end face of the honeycomb body to identify defective cells. Preferably, the step of detecting involves illuminating the particles. The illuminated particles are preferably then imaged.

Other features and advantages of the invention will be apparent from the following drawings, detailed description, and the appended claims.

DETAILED DESCRIPTION OF THE INVENTION

The invention will now be described in detail with reference to a few preferred embodiments, as illustrated in accompanying drawings. In the following description, numerous specific details are set forth in order to provide a thorough understanding of the invention. However, it will be apparent to one skilled in the art that the invention may be practiced without some or all of these specific details. In other instances, well-known features and/or process steps have not been described in detail in order to not unnecessarily obscure the invention. The features and advantages of the invention may be better understood with reference to the drawings, discussions, and claims that follow.

Apparatus embodiments of the invention provide a system for detecting defects in a honeycomb body having cells (or channels) that are selectively end-plugged, such as in diesel particulate filters. The interior walls and plugs of the honeycomb body are preferably porous. Thus, the porous walls and plugs are preferably tested for the presence of defects, in that any defect may be detrimental. The system includes an apparatus which substantially uniformly applies a flow velocity profile of a particulate fluid across a first end face of the honeycomb body, thereby allowing defects to be reliably detected throughout the honeycomb body.

Figure 5:
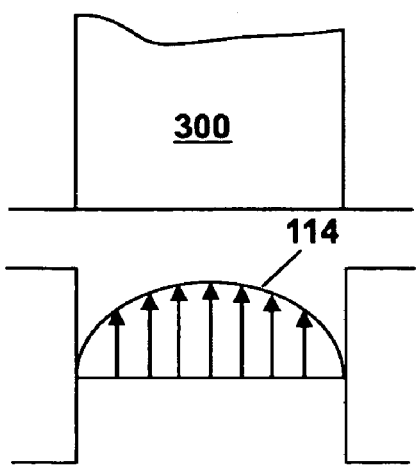
FIG. 5 is a graphical depiction illustrating a non-uniform flow velocity profile of a prior art apparatus.
Figure 6:
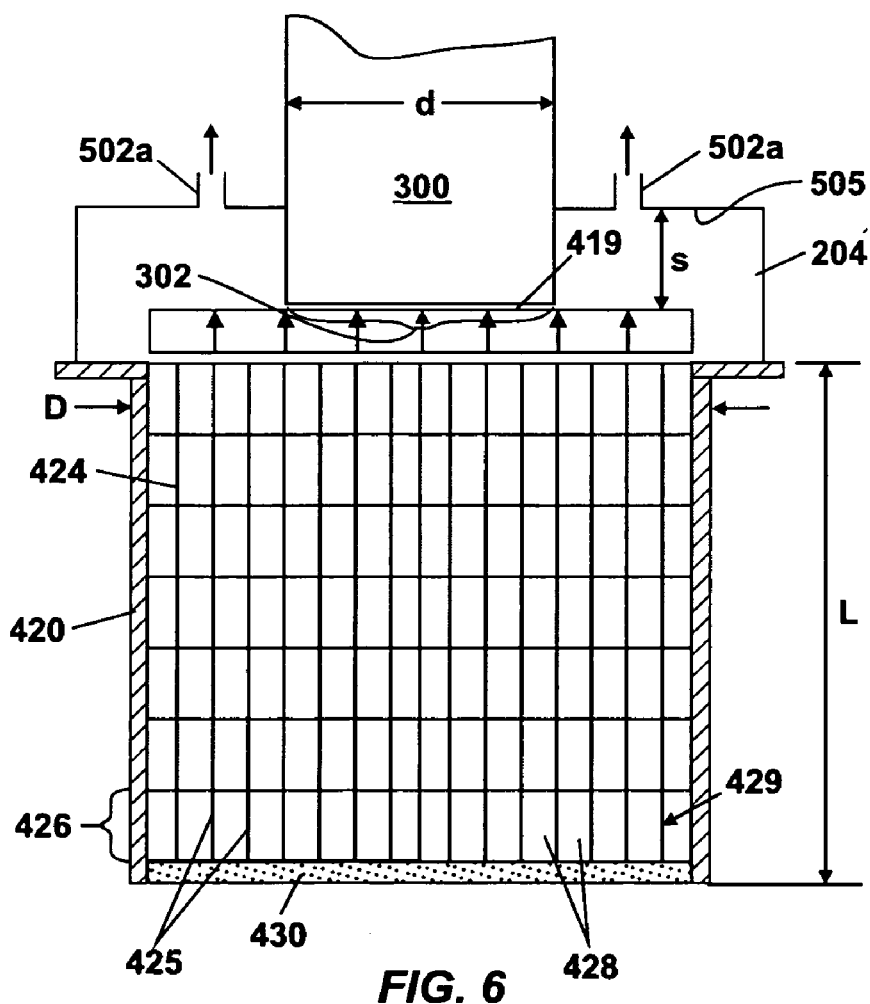
FIG. 6 is a partially cross-sectioned graphical depiction illustrating the substantially uniform flow velocity profile of the present invention.

It was recognized by the inventors that the accuracy of the detection technique depends, at least in part, on the consistency and uniformity of the particulates provided to the end face of the honeycomb body. In particular, the present invention solves the problem of a non-uniform flow profile 114 provided to the filter 300 by prior art apparatus (see FIG. 5) described in US Patent Application Publication 2003/0112437. In general, as best shown in FIG. 6, the present invention apparatus presents a substantially uniform velocity flow profile 419 of particulate fluid across a first end face 302 of the honeycomb body 300 (See FIG. 6)—the arrows of equal length indicating a substantially the same velocity provided across all portions of the honeycomb end 302. This is accomplished, according to one embodiment, by including a flow path, which is defined by a pipe 420, between a source of particulate fluid and the first end face 302 of the honeycomb body 300. The pipe 420 preferably includes a round cross-section (however, other cross-sectional shapes are possible, such as square, rectangular, etc.) and is preferably generally axially aligned with the honeycomb body 300. Further, preferably at least the inner dimension, D, (e.g., diameter) of the pipe 420 at the point where the particulate fluid is provided to the first end face 302 (near the pipe's upper end) is larger than a maximum transverse outer dimension, d, of the honeycomb 300. This feature improves the uniformity of the flow velocity profile 419 by reducing the effect of boundary layer flow on the distribution of the particulate fluid across the first end face 302 of the honeycomb body 300. In particular, the flow associated with the areas of the periphery of the pipe are preferably not directed toward the end face 302, such that only the centermost portion of the profile 419 is presented to the honeycomb 300.

According to a further aspect of the invention shown in FIG. 6, the apparatus may include a flow straightener 424 disposed in the flow path. The flow straightener 424 preferably comprises a plurality of flow vanes 425 which minimize and/or mitigate boundary layer influence of flow in the large pipe 420. In particular, the vanes 425 minimize the ability for a non-uniform flow profile to be developed in the pipe 420. In particular, the vanes 425 limit the ability for the particulate fluid to flow laterally (in a cross flow direction—perpendicular to an axial flow direction) within the pipe 420. This enables the provision of a substantially uniform flow velocity profile 419 across the first end face of the honeycomb body 300 (See FIG. 6). The vanes 425 are preferably parallel to one another and preferably interconnect to form a honeycomb member 429.

Figure 1:
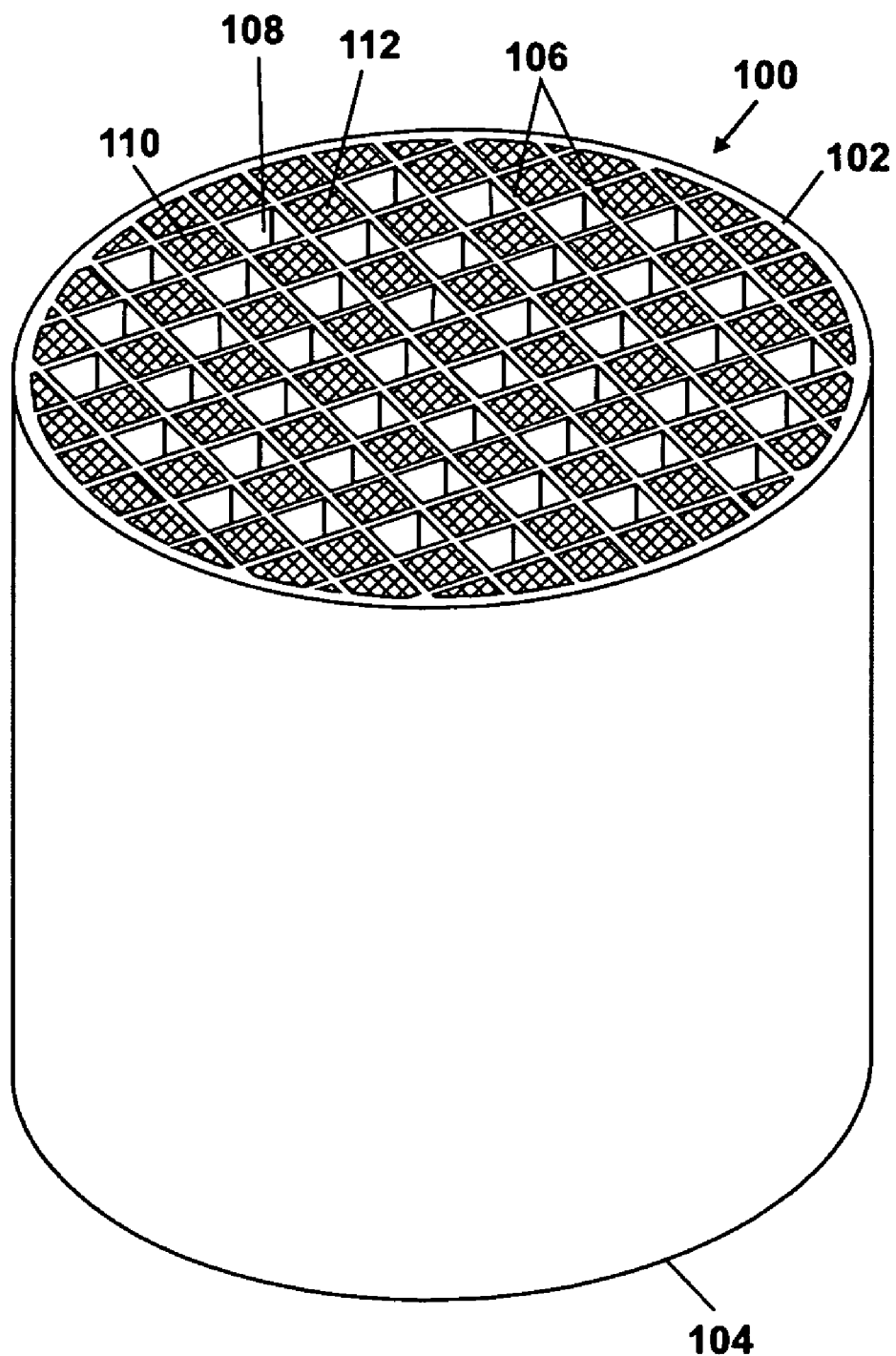
FIG. 1 shows an isometric view of a prior-art wall-flow honeycomb filter.
Figure 2A:
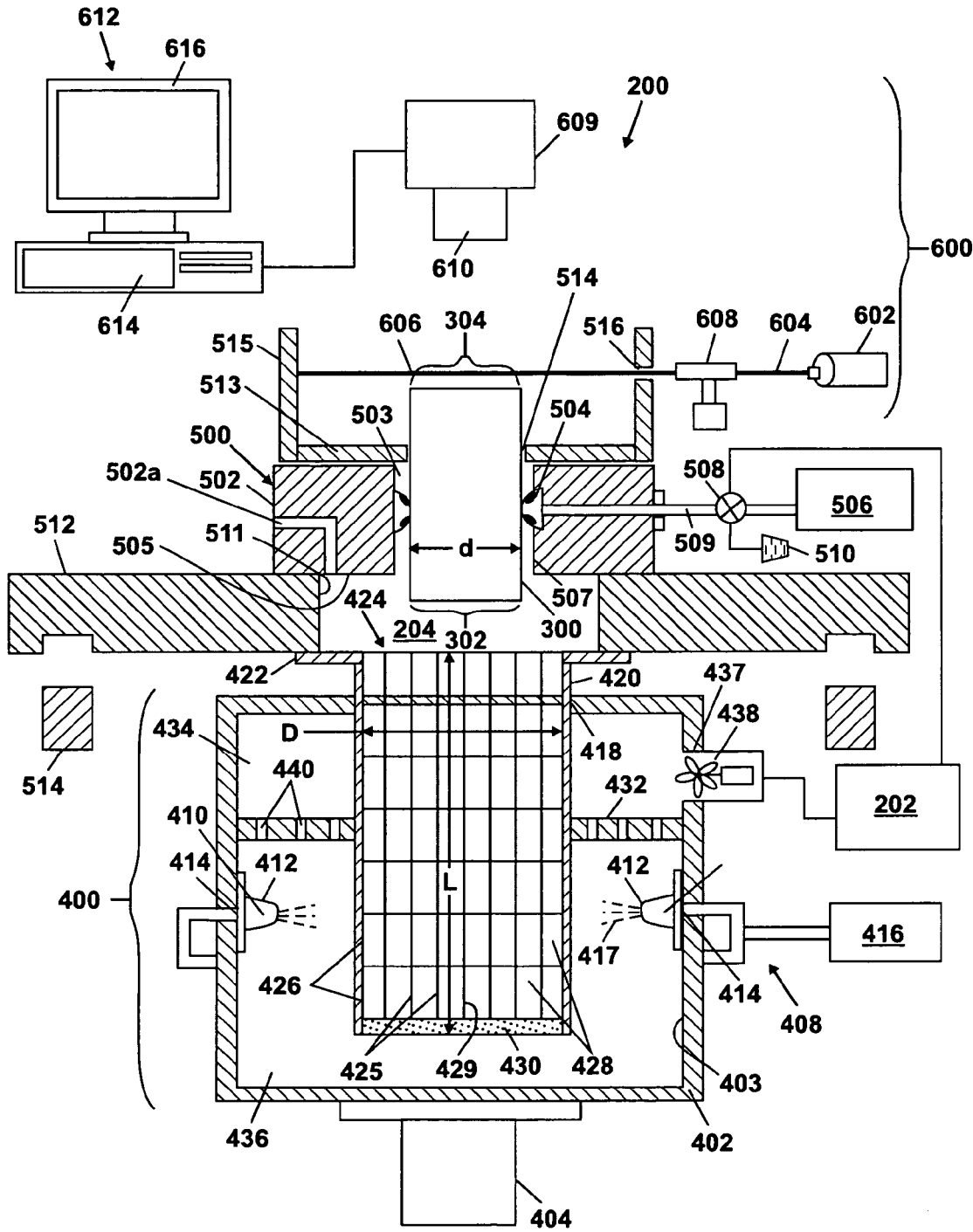
FIG. 2A shows a partially cross-sectioned view of a system apparatus for detecting defects in a honeycomb body according to embodiments of the invention.

FIG. 2A shows a detailed depiction of the system 200 for detecting defects in the honeycomb body 300 according to embodiments of the invention. The system 200 includes a particulate fluid source 400, a honeycomb holder 500, and a particulate detector 600. The particulate fluid source 400 produces a particulate fluid which is presented to the end face 302 of the honeycomb body 300 through a flow path. The particulate fluid is a solid or liquid particulates suspended in a gaseous medium. In one embodiment, the particulate fluid is a fine liquid particle mist, which may be generated by nebulizing or atomizing water or other liquid. A mist of water particles suspended in air is most preferable.

The honeycomb holder 500 holds the honeycomb body 300 in a suitable position to receive the flow of particulate fluid from the particulate fluid source 400. The particulate detector 600 illuminates the particulate fluid by projecting light, preferably in a plane, above an end face 304 of the honeycomb body 300. Most preferably, the detector captures an image of the position of particles illuminated due to interference of the light beam with the particulates emerging from the second end face 304 of the honeycomb body 300. The honeycomb body 300 is preferably positioned in the system 200 and the system is configured such that convection currents and eddy currents that may distort the flow of particulate fluid into the honeycomb body or flow of particulates out of the honeycomb body 300 is minimized or avoided.

The honeycomb body 300 is preferably a porous ceramic body formed of cordierite, aluminum titanate, or silicon carbide, for example, and is preferably formed by extrusion of a plasticized ceramic-forming batch material including pore formers (such as graphite or starch), cellulose material, and a solvent. The extruded honeycomb body is preferably fired to burn out the pore formers. Such firing is preferably performed before the testing the honeycomb body 300 for the presence of defects. However, it should be recognized that the present invention may be useful for detecting defects in green (unfired) honeycombs.

Figure 3:
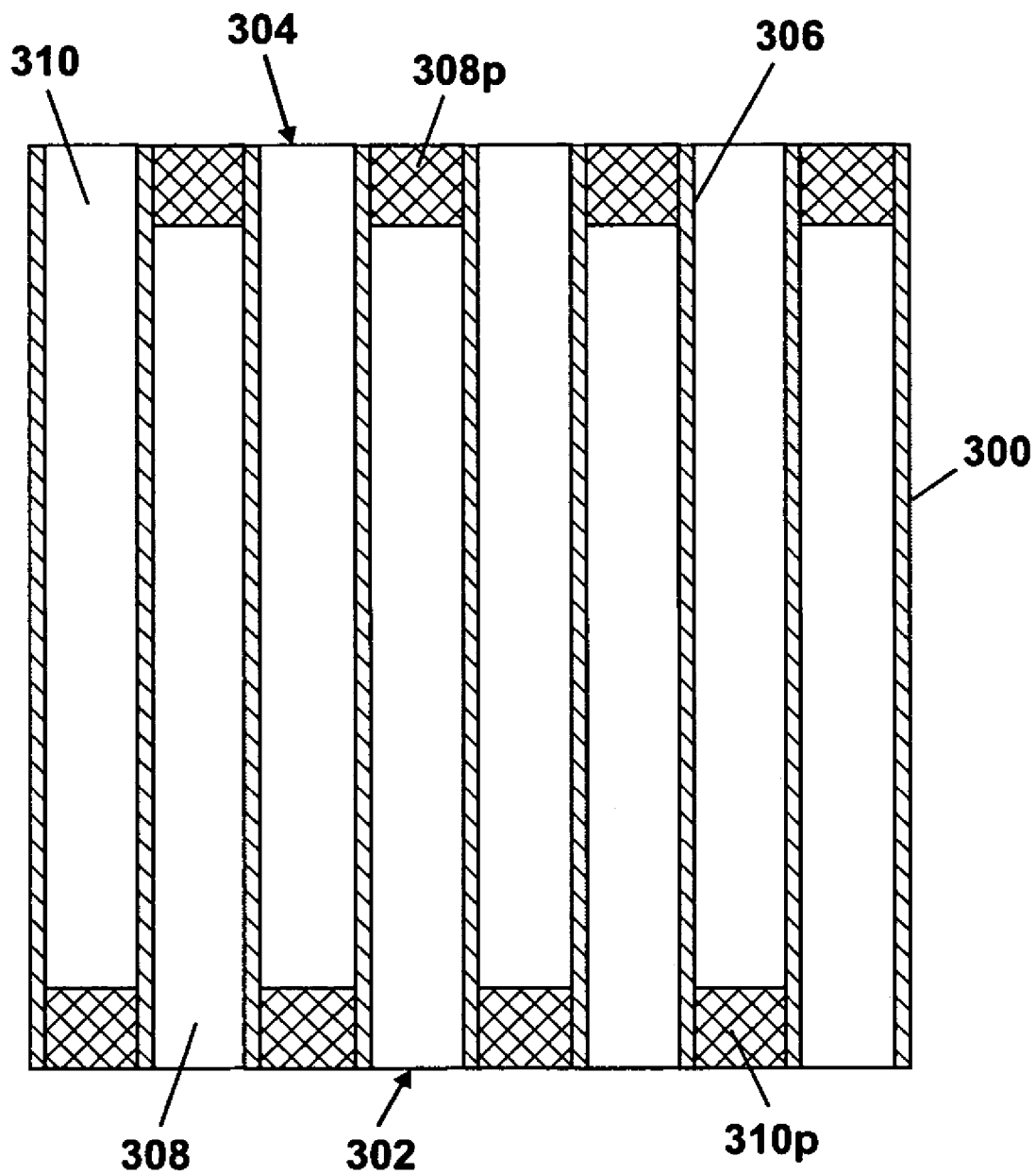
FIG. 3 is a cross sectional view of the honeycomb body of FIG. 2A.

FIG. 3 shows a side cross-sectional view of a typical honeycomb body 300 according to one embodiment of the invention. The honeycomb body 300 has end faces 302, 304 and preferably porous ceramic interior walls 306 extending between the end faces 302, 304. The walls 306 define inlet and outlet cells 308, 310. The inlet cells 308 are closed (plugged) with plugs 308p where they adjoin the end face 304 and are open where they adjoin the first end face 302. The outlet cells 310 are closed with plugs 310p where they adjoin the first end face 302 and are open where they adjoin the second end face 304. The plugs 308p, 310p may be made of a mixture of ceramic material, binder, and plasticizer and are preferably porous. Where the honeycomb body 300 is used as a wall-flow honeycomb filter, the thickness and porosity of the walls 306 are such that the structural integrity of the honeycomb body 300 is sufficient. For diesel exhaust filtration, the walls 306 may incorporate pores having mean diameters in the range of 1 to 60 μm, more preferably in a range of 10 to 50 μm, and porosities above 35%; more preferably between 40-65%, for example. Plugs exhibit similar porosities.

Again referring to FIG. 2A, the particulate fluid source 400 preferably includes a housing 402 forming an interior cavity 403. An actuator 404, such as a hydraulic or pneumatic cylinder, is coupled to the housing 402 such that the housing 402 is vertically movable, e.g., between a non-testing and a testing position. The particulate fluid source 400 further includes a particulate generator 408 which communicates with the interior cavity 403 of the housing 402. In the preferred embodiment, the particulate fluid used for testing is a suspension of fine drops of liquid in air, i.e., a mist or fog. For this embodiment, the particulate generator 408 is a device that generates the fine particle mist, such as a sprayer, nebulizer, atomizer, or humidifier. In one exemplary embodiment, the particulate generator 408 includes one or more nozzles 410 preferably mounted on the wall of the housing 402, such that their outlets 412 open into the interior cavity 403. The inlets 414 of the nozzles 410 are in fluid communication by conduits with a high pressure liquid source 416, such as liquid water. The nozzles 410 convert the liquid received from the liquid source 416 into a fine spray of particulate fluid 417 (preferably water particles suspended in air). Preferably, the particulate fluid is formed in the cavity as a dense fog.

Figure 7:
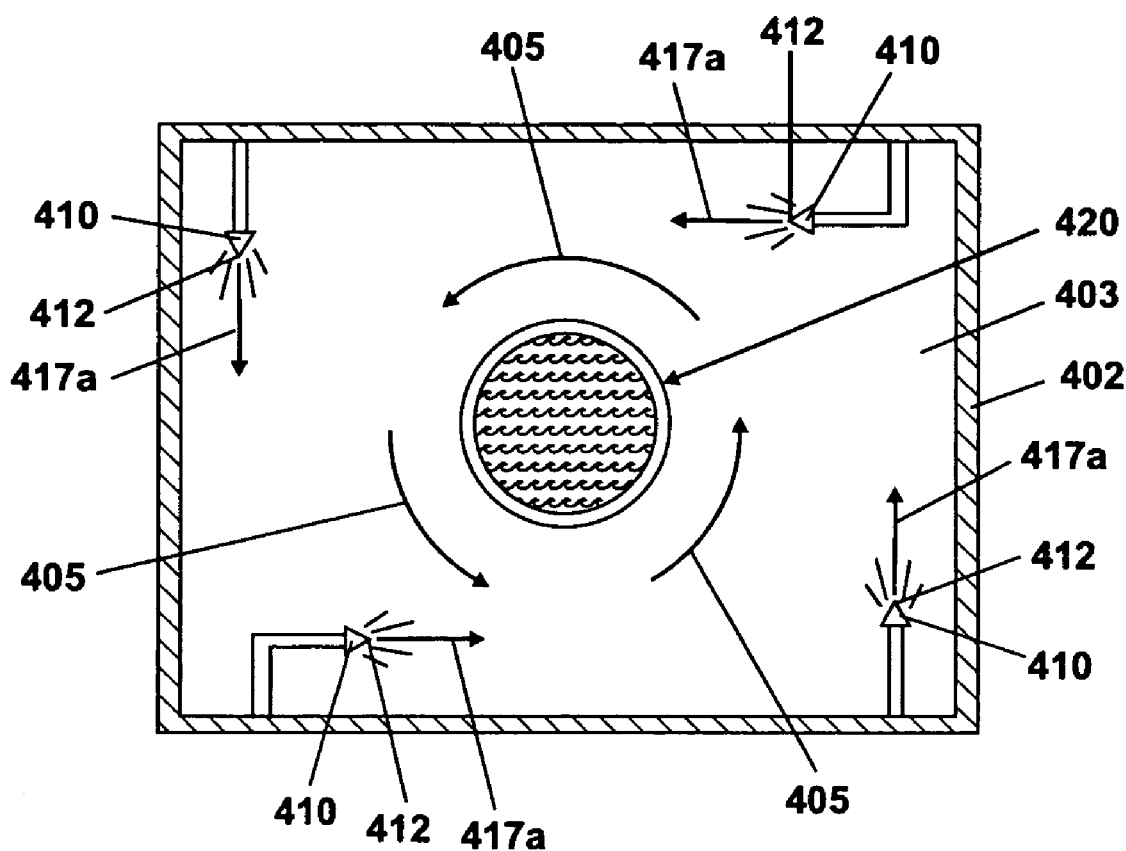
FIG. 7 is a bottom partially cross-sectioned view illustrating one embodiment of particulate generator of the present invention.

According to a further aspect of the invention, as best shown in FIG. 7, the ability to detect defects in the peripheral cells of the honeycomb article may be further enhanced by imparting a swirl pattern to the particulate fluid in the cavity 403 of the housing 402. The swirl pattern (having a rotational component) in the cavity 403, indicated by arrows 405, is preferably achieved by orienting the plurality of nozzles 410 such that they emit spray from their outlets 412 having a tangential component. In other words, the nozzles 410 are oriented such that their outlets 412 point substantially laterally within the housing 402. The nozzles 410 are preferably offset from the centerline of the pipe 420 and the spray trajectory, as indicated by arrows 417a, of each nozzle 410 is preferably generally tangential to the periphery of the pipe 420. For example, the nozzles 412 may be mounted near the corners of the housing 402 and include a spray trajectory 417a substantially along the sides of the housing. However, it should be recognized that any orientation or means that produces a swirl to the particulate fluid in the cavity 403 may be employed.

The particulate fluid source 400 is interconnected with a flow path, preferably by a pipe 420, inserted in an opening 418 at the top of the housing 402. The upper end of the pipe 420 extends out of the housing 402 and is preferably terminated at a flange 422. The pipe 420 may be secured in the opening 418 by any suitable means, such as glue or fasteners. The pipe 420 defines the flow path for the particulate fluid 417 between the interior cavity 403 of the particulate fluid source and the first end face 302 of the honeycomb body 300. The pipe 420 is preferably cylindrical and straight. In a preferred embodiment, the inner dimension, D, (e.g., diameter) of the pipe 420 at the point where the particulate fluid exits the pipe 420 is larger than the maximum outer dimension, d, (e.g., the diameter of a round body, or the longest transverse dimension of an non round body) of the honeycomb body 300. In some embodiments, the inner dimension, D, of the pipe 420 at the exit point is at least 30% larger than the maximum outer dimension, d, of the honeycomb filter 300; more preferably at least 50% larger; and most preferably at least 75% larger. In general, the inner diameter of the pipe 420 is selected such that boundary layer flow does not have a significant effect on the distribution of particulate fluid across the end face 302 of the honeycomb body 300. In one embodiment, the length, L, and inner dimension, D, (e.g., diameter) of the pipe 420 are selected such that the flow regime presented to the end face 302 is substantially laminar. In particular, it is preferable that the L/D ratio preferably be between 0.25 and 1.5, for example. During testing, the pipe 420 is generally axially aligned with the honeycomb body 300 so as to present the most uniform flow profile to the first end face 302.

Figure 4A:
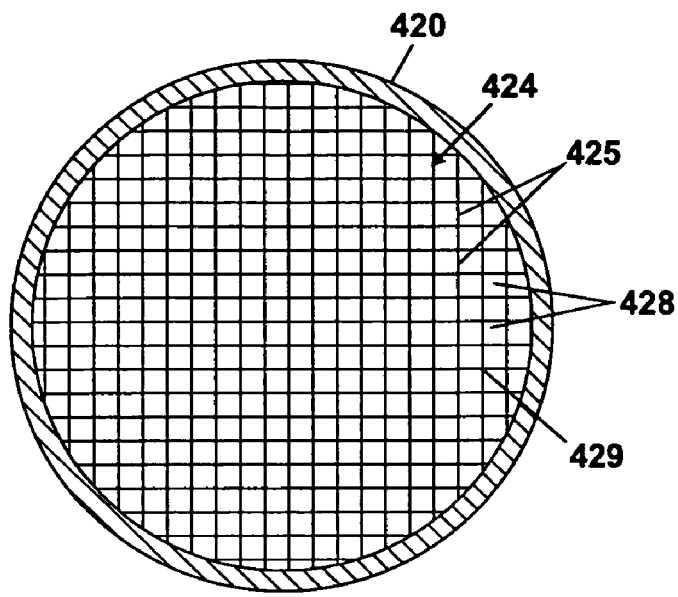
FIG. 4A is an end view of one configuration of the flow straightener of FIG. 2A.
Figure 4B:
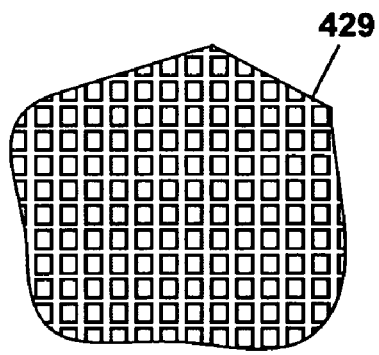
FIGS. 4B-4E are partial end views illustrating alternative configurations of the flow straightener of FIG. 2A.
Figure 4C:
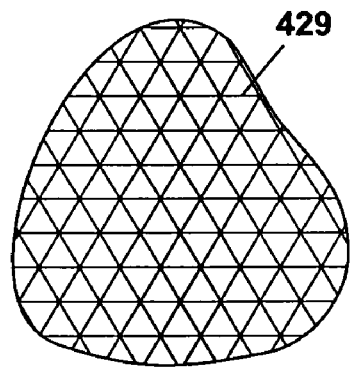
Figure 4D:
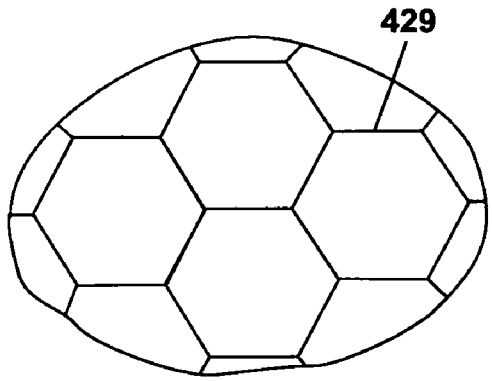
Figure 4E:
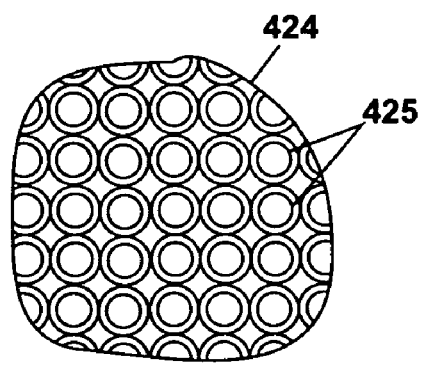

According to a preferred aspect of the invention, the flow path further includes a flow straightener 424 (e.g., disposed in the pipe 420). As shown in FIGS. 2A, 4A and 6, the flow straightener 424 is positioned in the pipe 420 and forms a plurality of flow passages 428, which are preferably parallel to each other in the axial direction. The straighteners interact to substantially prevent lateral flow of the particulate fluid, i.e., minimize/mitigate boundary layer influence of pipe, as the particulate fluid passes through the pipe 420. In one embodiment, the flow straightener 424 includes a plurality of flow vanes 425, which are preferably parallel to each other in the axial flow direction. Most preferably the vanes 425 are interconnected (as shown in bottom views FIG. 4A-4D) to form a honeycomb member 429 and, thus, form the plurality of smaller flow passages 428 within the pipe 420. More preferably, the flow straightener 424 may include more than one honeycomb member 429, in particular, an axial stack of honeycomb discs 426 (See FIGS. 2A and 6) which are stacked in the pipe 420. Preferably, the vanes 425 extend entirely across the inner dimension of the pipe 420. The honeycomb discs 426 have cells (or channels) 428 which, when stacked, may be aligned or staggered. Moreover, the cell density of each of the honeycomb discs 426 may or may not be the same. In one embodiment, the number of the cells 428 per area is larger than number of the cells 308, 310 per area in the honeycomb filter 300. Most preferably, the honeycomb member 429 includes a cell density of greater than 1 cells/in² (0.15 cells/cm²); more preferably between 4 and 64 cells/in² (0.62 to 9.92 cells/cm²). To eliminate water blockage, most preferably the cell density is less than 16 cells/in² (0.62 to 2.48 cells/cm²). The honeycomb discs 426 may be made of any suitable material, e.g., a metal, plastic, glass, composite, or ceramic. Further, the honeycomb members 429 may include any number of cell configurations, such as rectangular (FIG. 4B), triangular (FIG. 4C), hexagon (FIG. 4D), or square (FIG. 4a). Aluminum hexagonal honeycomb discs are preferred. However, it should be recognized that any configuration that provides a plurality of flow passages may be employed. For example, the flow straightener 424 may include vanes 425 formed from a plurality of stacked tubes as shown in FIG. 4E. Any suitable other structures capable of providing multiple parallel flow passages in the pipe may be used as well. Preferably, the flow straightener 424 is positioned within and fills substantially an entire length, L, of the pipe 420. Preferably, each of the flow passages includes a length to transverse dimension ratio of greater than 10.

In one embodiment, as best shown in FIGS. 2A and 6, a porous media 430, such as a fibrous material, is mounted adjacent to and positioned at an inlet of the flow straightener 424. The porous media 430 may control the size of particulates entering the flow straightener 424. In general, it is desirable that the size of the particulates used in testing is in a range from 1 to 50 μm, preferably in a range from 1 to 30 μm, more preferably in a range from 1 to 10 μm.

In a preferred implementation, a partition 432 is disposed inside the housing 402 and about the pipe 420 such that an upper chamber 434 and a lower chamber 436 are formed and defined inside the interior cavity 403 of housing 402. The partition 432 includes orifices 440 which allow fluid communication and flow between the upper chamber 434 and the lower chamber 436. The lower chamber 436 contains the particulate fluid generated by the particulate generator 408. The upper chamber 434 contains pressurized air and is substantially devoid of the particulate. The pressurizing of the air is provided by a blower 438 mounted in an opening 437 in the upper chamber 434. The blower 438 may be controlled by a control unit 202. The blower 438 maintains a pressure differential between the upper chamber 434 and atmospheric room pressure (outside the housing) which causes air to flow from the upper chamber 434 to the lower chamber 436 and prevents particulate fluid from flowing from the lower chamber 436 to the upper chamber 434 through the orifices 440. The pressure differential is preferably less than 0.5 in. H₂O during testing. However, it should be recognized that the pressure required for good detection is dependent on the part size, geometry, and porosity. The applied pressure differential is set by routine experimentation until the optimum detection is achieved. The orifices 440 are arranged in the plate 432 such that the air flow is substantially evenly distributed across the lower chamber 436. The air forced into the lower chamber 436 drives the particulate fluid in the lower chamber 436 up through the flow path including the flow straightener 424 to provide a substantially uniform flow profile to the end 302 of the honeycomb 300. The term "substantially uniform" flow profile as used herein means that the flow velocity at any point along the bottom end of the article 300 in a longitudinal direction of the article varies by no more than 25%; more preferably less than 20%; and most preferably less than 10%. In particular, the present invention advantageously may provide a flow velocity of the particulate fluid at the periphery of the article 300 which is substantially equal to the flow velocity of the particulate fluid at the center of the article 300.

The honeycomb holder 500 includes a fixture 502 having an opening 503 for receiving the honeycomb body 300. An inflatable bladder 504 is fitted in an inner wall 507 of the fixture 502. A flow line 509 supplies pressure to the bladder 504 from a fluid pressure source 506, or exhausts pressure to an exhaust 510 thereby allowing fluid to be supplied or discharged from the bladder 504, as needed. The fluid may be air or other suitable fluid for inflating the bladder 504. A valve 508 is disposed in the flow line 509 to control communication between the fluid pressure source 506, the bladder 504, and exhaust 510. The opening and closing of the valve 508 is preferably controlled by a suitable control unit 202, which may also control the pressure supplied to the particulate fluid. When the valve 508 is open, pressurized fluid can flow from the fluid pressure source 506 into the bladder 504, thereby inflating the bladder 504 such that it engages the honeycomb body 300 to secure the part within the holder. However, it should be recognized that the invention is not limited to use of an inflatable bladder 504 to secure the honeycomb body 300 to the fixture 502. Alternatively, clamps or other suitable mechanisms may be used to secure the honeycomb body 300 to the fixture 502.

The fixture 502 is supported on a platform 512. The platform 512 has an opening 511 which is aligned with the opening 503 in the fixture 502. When not testing, the platform 512 usually rests on rails 514. The housing 402 can be moved upwardly by the actuator 404 until the flange 422 of the pipe 420 engages the platform 512. Further upward motion of the housing 402 would then lift the platform 512 off the rails 514 to a position where testing can be performed. In particular, it is desired that when the flange 422 engages the platform 512, the bottom end of the fixture 502, the inner wall of the platform 512, and the upper end of the housing 502 form a chamber 204 adjacent to the exit end of the pipe 420.

As best shown in FIGS. 2A and 6, in a preferred embodiment, the lower end of the honeycomb body 300 preferably extends into the chamber 204 by a predefined amount, S. This is so that inlet end face 302 of the honeycomb body 300 is exposed to free flow of particulate fluid exiting from the pipe 420 rather than eddy currents that may develop at the boundary of the cavity 204. This aspect of the invention is believed to further improve the uniformity of the particulate fluid flow through the honeycomb 300. Optionally, ports 502a may be provided in the fixture 502 (or the platform 512) through which fluid at the boundary of the chamber 204 can be extracted using, for example, a vacuum pump, or can escape naturally (as indicated by arrows in FIG. 6).

The inventors herein further discovered that there is a tendency for convection currents to form around the outlet end face 304 of the honeycomb body 300, for example due to temperature gradients between the room environment and the honeycomb body 300. Such convection currents can laterally deflect flow of particulates emerging from the honeycomb body 300 such that it is difficult to accurately locate any defective cells through which the particulates have emerged. In order to inhibit the convection currents around the outlet end face 304, one example embodiment of the present invention includes a convection current shield 513. In a preferred embodiment, the convection current shield 513 may be stationarily mounted. When the fixture 502 is raised in operation, the second end face 304 of the honeycomb 300 extends through an opening 514 in the shield 513 such that the upper end of the honeycomb body 300 is positioned above the shield 513 in the test position. The opening 514 of shield 513 is sized and shaped such that it conforms closely to the periphery of the honeycomb body 300, preferably with no more than a ½ inch (12.7 mm) gap around the body 300. Extension of the upper end 304 of the honeycomb body 300 through and above the convection current shield 513 and close fitting of the opening 514 around the honeycomb body 300 act together to inhibit formation of convection currents around the outlet end face 304. Shield 513 may preferably have appended thereto vertical walls 515 to further inhibit air flows from the room environment. Preferably, the apparatus 200 is housed within a larger chamber (not shown).

The particulate detector 600 detects the presence of, and location of, defective cells/plugs. Most preferably, the detector 600 includes a light source 602 for generating a light beam 604 adjacent to the outlet end of the honeycomb. One example of a light source 602 is a laser. The laser source preferably cooperates with optical elements, such as rotating faceted mirror 608, to converting the light beam 604 to the planar sheet of light 606. The mirror 608 is preferably rotating at greater than 500 rpm and has preferably 10 facets. The spinning mirror deflects the beam 604 through an angle of about 72 degrees, and, thus, produces a plane of light 606 large enough to fully span across the end 304 of honeycomb 300. Optionally, more than one light source may be needed to form a uniform, preferably planar, sheet of light 606 across the outlet end face 304 of the honeycomb body 300, for example, as taught in U.S. Provisional Patent Application 60/638,201 filed on Dec. 21, 2004 by L. Zoeller, III and entitled "Method and System for Identifying Defective Cells in A Plugged Honeycomb Structure."

The sheet of light 606 is preferably formed above the convection current shield 513 and generally perpendicular to the outlet end face 304. Alternatively, it may be desirable to control the spread of the sheet of light 606. In which case, a slot 516 may be formed in the uprights 515 through which the light sheet 606 extends and is projected above the outlet end face 304. The width of the slot 516 is selected to control spread of the sheet of light 606. Preferably, the distance between the sheet of light 606 and the outlet end face 304 is such that the particulates emerging from the outlet end face 304 still have sufficient momentum to intersect the planar sheet of light 606. Thus, the sheet of light 606 should be as close as possible to the end face 304 without interfering with the end face 304. In one embodiment, the distance between the sheet of light 606 and the outlet end face 304 is in a range from 1/16 in. (1.6 mm) to ½ in. (12.7 mm). It should be recognized that white light sources may be used as well, provided a well defined plane of light is formed. Other forms of detectors may also be utilized.

The particulate detector 600 further preferably includes an imaging device 609, such as a camera or camcorder, positioned above the outlet end face 304 of the honeycomb filter 300. The imaging device 609 captures an image of any illuminated particles flowing out of the face 304. In particular, the areas where defects are indicated show up as bright spots in the image. In the case of a single defect, the bright spot is a dot substantially directly above the cell that has the increased particulate fluid flow (due to the defect). Thus, the location can be immediately identified for plugging. The particulate detector 600 may further include an optical system 610, such as lenses, for focusing the illuminated region on the imaging device 609. The imaging device 609 may include an internal processor which processes information collected by the device into image files and stores the image files in memory in the device. The processor may support various types of image file formats, such as TIFF and JPEG. The imaging device 609 may be coupled to a computer system 612 (not drawn to scale). The computer system 612 may include a processor 614 and video monitor 616 and other peripheral devices necessary for interacting with the system, such as a keyboard and mouse. These peripheral devices are well known in the art and will not be discussed further. The image files stored on the memory in the image device 609 can be transferred to the processor 614 for further processing. The image files may also be displayed on the video monitor 616.

The imaging device 609 may be capable of detecting colors other than white light. For example, the imaging device 609 may be capable of detecting one or more colors selected from, for example, red, blue, and green. In the latter case, the sheet of light 606 may have a color that may be suitably detected by the imaging device 609, for example red. Since the sheet of light 606 is positioned above the outlet end face 304, particulates emerging at the outlet end face 304 would intersect the sheet of light 606, scattering the sheet of light 606 and illuminating the particles at the locations where they intersect with the sheet of light 606.

Figure 2B:
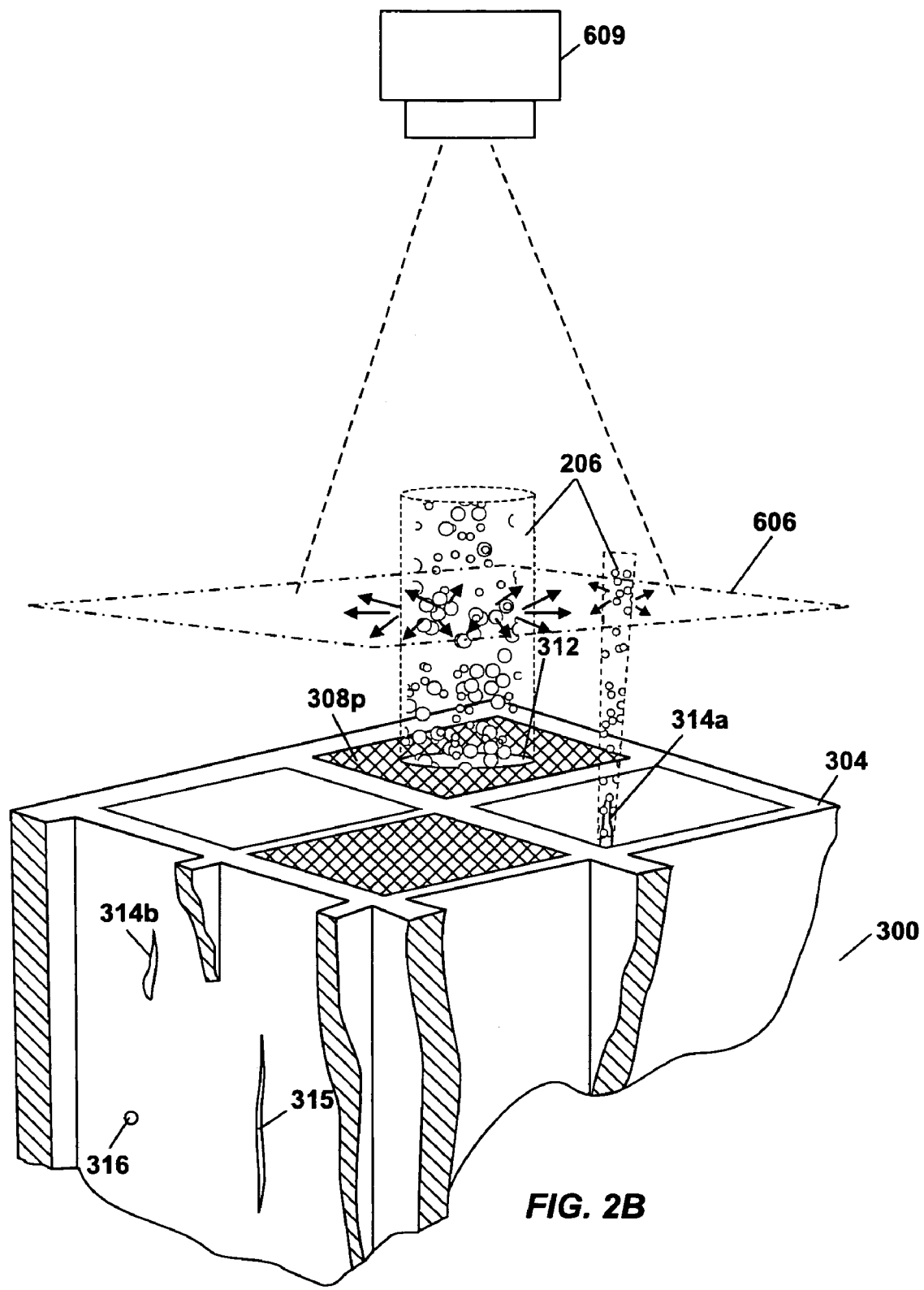
FIG. 2B is a partial isometric view showing particulates emerging from defective cells (from plug or wall defects) in a honeycomb body.

For illustration purposes, FIG. 2B shows defects 312, 314a, 314b, 315, and 316 in the honeycomb body 300. Defect 312 is a hole or other defect in a plug 308p, such as a partial fill or crack. Defects 314a, 314b are tears in the interior walls 304 (only a few shown for clarity) of the honeycomb body 300 resulting from extrusion or processing. Defect 315 is a crack in a wall of the honeycomb body 300 (which may be may interior or exterior wall). Defect 316 is a hole in a wall of the honeycomb body 300 resulting from pore former burnout. For illustration purposes, particulates 206 are shown emerging from the defects 312, 314a. The particulates 206 are shown intersecting with and scattering the sheet of light 606 and illuminating the particles 206 in the particulate fluid. The imaging device 609 can be operated to capture an image of the reflected (scattered) beams and illuminated particles 206. Cells in the honeycomb body 300 having defects would discharge more particulates and larger particulates than cells not having defects. Thus, cells having defects can appear as brighter or colored spots in the image captured by the imaging device. The size of the spots can provide an indication of the size of the defects in the honeycomb filter 300. If the image appears uniform, then there are no defects in the honeycomb filter 300. The location of the brighter or colored spots can be used to identify the location of the defects in the honeycomb filter 300.

Returning to FIG. 2A, the particulate source 400 is raised such that the flange 422 engages the platform 512. The particulate source 400 is further raised such that the platform 512 is lifted off the rails 514 and the honeycomb 300 is inserted through convection current shield 513 and is raised to the position where the end face 304 is appropriately positioned slightly below the light plane 606, as described above. Particulate fluid which is generated inside the lower chamber 436 as previously described is provided to the flow path. The blower 438, used to create a differential pressure between the upper chamber 434 and the lower chamber 436, drives the particulate fluid in the lower chamber 436 up through the tube 420 and flow straightener 424. The flow straightener 424 minimizes or mitigates boundary layer influence of large pipe as the particulate fluid passes through the pipe 420 to the cavity 204. Thus, upon exit from tube, the end face 302 of the honeycomb body 300 is exposed to a substantially uniform velocity flow profile of the particulate fluid. Additionally, effects of eddy currents on distribution of the particulate fluid across the end face 302 are further minimized by placing the end face 302 in the free flow of particulate fluid by spacing the lower end face 302 away from the immediately adjacent under surface of the fixture 502. Typically, as shown in FIG. 6, the end face 302 is spaced from the surface 505 by a distance, S, of ¼ inch (6.35 mm) or more; and more preferably ½ inch (12.70 mm) or more.

Typically, the particulate fluid would enter into the honeycomb body 300 through the inlet cells which are not end-plugged at the inlet end face 302. If there are defects in the cells in the honeycomb body 300, the particulates in these defective cells would readily flow through the defects into adjacent cells or through the plug and emerge at the outlet end face 304, intersecting and scattering the sheet of light 606 formed above the outlet end face 304. The reflected beams produced by the scattering and the illuminated particles are imaged by the imaging device 609. The image captured by the imaging device 609 can be interpreted to determine the location of the defective cells and size of the defects, and any defects found can be repaired. To facilitate location of defective cells, it may be desirable to also image a surface of the outlet end face 304 of the honeycomb body 300. The surface image would show the location of cells in the honeycomb body 300.

One advantage of the present invention is that ambiguity in integrity testing of honeycomb body using a particulate fluid can be avoided. This is achieved, in one embodiment, by providing a uniform flow velocity to the particulate fluid such that the flow is substantially the same across the end face of the honeycomb body. In particular, the invention is useful for determining and locating defective cells around the periphery of the body. The particulate source according to an embodiment of the invention can be used when defects are detected by a method including monitoring or imaging of the properties of particulates emerging from an end face of the honeycomb body. However, use of the particulate generator is not limited to this method. The particulate generator can also be used when defects in a honeycomb body are detected by monitoring infrared emissions from an end face of the honeycomb body from which particulates emerge. In general, the particulate generator is useful whenever the method of detecting defects in a honeycomb body includes passing a particulate fluid through the honeycomb body and monitoring, using any suitable method, particulates emerging from an end face of the honeycomb body.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A system for detecting defects in a honeycomb body, comprising:
   a fixture adapted to hold the honeycomb body;
   a particulate fluid source;
   a flow path for particulate fluid between the particulate fluid source and an inlet end face of the honeycomb body, the flow path defined by a pipe positioned between the particulate fluid source and the inlet face of the honeycomb body, and
   a flow straightener including a plurality of vanes disposed in the pipe, the flow straightener and pipe terminating adjacent and prior to the inlet end face of the honeycomb body.

2. The system of claim 1 wherein an inner dimension of the pipe at a point where the particulate fluid exits the pipe is larger than a maximum transverse outer dimension of the honeycomb body.

3. The system of claim 1 wherein the plurality of vanes of the flow straightener form a plurality of flow passages.

4. The system of claim 3 wherein the flow passages are provided by a honeycomb member.

5. The system of claim 4 wherein the honeycomb member further comprises stacked honeycomb discs.

6. The system of claim 1 further comprising porous media mounted adjacent to the flow straightener.

7. The system of claim 1 wherein the plurality of vanes of the flow straightener are included along substantially an entire length of the pipe.

8. The system of claim 1 wherein the particulate fluid source comprises a particulate generator having one or more spray nozzles.

9. The system of claim 1 wherein the particle fluid source comprises a particulate generator oriented to have a substantially tangential particle trajectory.

10. The system of claim 1 wherein a length, L, and an inner diameter, D, of the pipe are selected such that L/D is between 0.25 and 1.5.

11. The system of claim 1 wherein the inlet end face is exposed to a flow of particulate fluid from the flow path having a substantially uniform velocity flow profile.

12. The system of claim 11 wherein the substantially uniform velocity profile varies by no more than 25% across an area defining the inlet end face.

13. The system of claim 1 wherein the inlet end face is spaced a distance, S>6 mm, relative to a surrounding underside of the fixture.

14. The system of claim 1 further comprising a convection current shield positioned above the fixture having an opening shaped and sized to conform substantially to an outer profile of the honeycomb body.

15. The system of claim 1 further comprising a detection system for monitoring particulate fluid emerging at an outlet end face of the honeycomb body.

16. The system of claim 15 wherein the detection system comprises a light source which projects a light beam adjacent the outlet end face of the honeycomb body.

17. The system of claim 15 wherein the detection system further comprises an imaging device which captures an image of illuminated particulates.

18. The system of claim 1 wherein a chamber is formed adjacent an exit end of the flow path and the chamber includes at least one port through which particulate fluid at the boundary of the chamber is withdrawn or can escape.

19. The system of claim 1 wherein the particulate fluid is a particulate water mist.

20. An apparatus for applying particulate fluid across an inlet end face of a honeycomb body, comprising:
    a particulate fluid source having a housing with an interior cavity, and a particulate generator which produces particulate fluid;
    a pipe disposed in the housing and having a first end open to the interior cavity and a second end wherein a pressure differential drives particulate fluid into the pipe; and
    a flow straightener comprising a plurality of flow vanes disposed in the pipe and terminating at the second end of the pipe, wherein the pipe and flow straightener are configured to direct the particulate fluid to the inlet end face of the honeycomb body.

21. The apparatus of claim 20 further comprising a partition disposed in the housing, the partition dividing the cavity into a first chamber and a second chamber.

22. The apparatus of claim 20 wherein flow passages are provided by an intersection of the plurality of flow vanes.

23. The apparatus of claim 20 wherein flow passages are provided by a honeycomb member.

24. The apparatus of claim 23 further comprising a stack of honeycomb discs.

25. The apparatus of claim 24 further comprising porous media mounted at an end of the flow straightener.

* * * * *